(12) United States Patent
de Beer

(10) Patent No.: US 9,913,949 B2
(45) Date of Patent: Mar. 13, 2018

(54) NEEDLE HUB ASSEMBLY FOR A SYRINGE AND A SYRINGE COMPRISING SUCH NEEDLE HUB ASSEMBLY

(71) Applicant: TSK Laboratory Europe B.V., Oisterwijk (NL)

(72) Inventor: Isodoris Angelinus Quirinus Maria de Beer, Oisterwijk (NL)

(73) Assignee: TSK Laboratory Europe B.V., Oisterwijk (NL)

( * ) Notice: Subject to any disclaimer, the term of this patent is extended or adjusted under 35 U.S.C. 154(b) by 125 days.

(21) Appl. No.: 15/028,559

(22) PCT Filed: Oct. 28, 2014

(86) PCT No.: PCT/NL2014/050743
§ 371 (c)(1),
(2) Date: Apr. 11, 2016

(87) PCT Pub. No.: WO2015/065177
PCT Pub. Date: May 7, 2015

(65) Prior Publication Data
US 2016/0279345 A1    Sep. 29, 2016

(30) Foreign Application Priority Data
Oct. 29, 2013  (NL) .................................. 2011699

(51) Int. Cl.
*A61M 5/32* (2006.01)
*A61M 5/00* (2006.01)
(Continued)

(52) U.S. Cl.
CPC ...... *A61M 5/3293* (2013.01); *A61M 5/31511* (2013.01); *A61M 5/002* (2013.01);
(Continued)

(58) Field of Classification Search
CPC .. A61M 5/3204; A61M 5/3293; A61M 5/345; A61M 2005/3206; A61M 2005/3208; A61M 2005/323; A61M 2005/3253; A61M 2005/3275; A61M 2005/3276; A61M 5/34; A61M 5/343; A61M 2005/31516; A61M 5/002; A61M 5/346
See application file for complete search history.

(56) References Cited

U.S. PATENT DOCUMENTS 4,078,565 A    3/1978 Genese
4,215,701 A    8/1980 Raitto
(Continued)

FOREIGN PATENT DOCUMENTS

WO    WO-03018091 A2    3/2003
WO    WO-2009144583 A1   12/2009
WO    WO-2015065177 A1    5/2015

OTHER PUBLICATIONS

"International Application Serial No. PCT/NL2014/050743, International Search Report dated Dec. 19, 2014", 5 pgs.
(Continued)

*Primary Examiner* — Quynh-Nhu H Vu
(74) *Attorney, Agent, or Firm* — Shwegman Lundberg & Woessner, P.A.

(57) ABSTRACT

Needle hub assembly (200) for a syringe (100), said assembly having a longitudinal axis (L1) comprising:—a needle hub body (210) having a syringe connector (212) for receiving an attachment member (110) of a syringe (100) at a first end (210a) of the body (210) and a needle receiving portion (214) at a second opposing end (210b) of the body (210),—a needle (216) extending from the needle receiving portion (214), wherein the syringe connector (212) comprises a substantially conical receiving opening (218) for receiving a syringe attachment member (110), at least a distal end (110b) thereof, wherein a length (A) of said opening (218), measured along the longitudinal axis (L1), is approximately 6.1+0.05 mm.

18 Claims, 3 Drawing Sheets

(51) Int. Cl.
*A61M 5/315* (2006.01)
*A61M 5/34* (2006.01)

(52) U.S. Cl.
CPC ... *A61M 5/346* (2013.01); *A61M 2005/31516* (2013.01); *A61M 2202/20* (2013.01)

(56) References Cited

U.S. PATENT DOCUMENTS

| | | | |
|---|---|---|---|
| 5,782,803 A * | 7/1998 | Jentzen | A61M 5/31511 604/110 |
| 5,964,737 A * | 10/1999 | Caizza | A61M 5/34 604/187 |
| 2003/0018301 A1 | 1/2003 | Sheppard et al. | |
| 2006/0276755 A1 * | 12/2006 | Sullivan | A61M 5/2448 604/187 |
| 2007/0197977 A1 * | 8/2007 | Shue | A61M 5/31511 604/218 |
| 2010/0152679 A1 * | 6/2010 | Tezel | A61M 5/347 604/241 |
| 2012/0245564 A1 | 9/2012 | Tekeste et al. | |

OTHER PUBLICATIONS

"International Application Serial No. PCT/NL2014/050743, Written Opinion dated Dec. 19, 2014", 6 pgs.

* cited by examiner

NEEDLE HUB ASSEMBLY FOR A SYRINGE AND A SYRINGE COMPRISING SUCH NEEDLE HUB ASSEMBLY

PRIORITY APPLICATIONS

This application is a U.S. National Stage Filing under 35 U.S.C. 371 from International Application No. PCT/NL2014/050743, filed on 28 Oct. 2014, and published as WO 2015/065177 on 7 May 2015, which claims the benefit of priority to The Netherlands Application No. 2011699, filed on 29 Oct. 2013; which applications and publication are incorporated herein by reference as if reproduced herein and made a part hereof in their entirety, and the benefit of priority of each of which is claimed herein.

FIELD OF THE INVENTION

The present invention relates to the field of dosage devices such as syringes, and more in particular to a needle hub assembly for a syringe suitable for, inter alia, the injection of fluids in medical applications, and the dosing of chemicals in non-medical applications.

BACKGROUND

Botulinum toxin, popularly known by one of its trade names, Botox, is a protein and neurotoxin that is used in various cosmetic and medical procedures. In cosmetic applications, a botulinum toxin injection may be used to prevent the development of wrinkles by paralyzing facial muscles. In non-cosmetic applications, botulinum toxin may be used to treat conditions of excessive and inappropriate muscle contraction, migraine, spasticity (persistent states of muscle contraction), sphincter contraction, eye-movement disorders, tics and tremors.

Botulinum toxin is administered to a patient by means of an injection using a suitable syringe with a needle hub assembly. The needle of the needle hub assembly is passed through the skin to reach subcutaneous tissue and subsequently, the botulinum toxin is injected by pushing the plunger of the syringe inside the barrel of the syringe such that the toxin is expelled from the syringe at the distal end thereof via the needle hub assembly.

SUMMARY OF THE INVENTION

Syringes used to administer botulinum toxin injections normally comply with ISO standards. This enables the use of every suitable needle hub assembly with every suitable syringe to inject the botulinum toxin.

However, although certain properties of the respective needle hub assembly and the syringe are standardized, the used needle hub assembly and the used syringe do not need to be designed for optimal use of the fluid inside the syringe. This means that, for instance when using a certain needle hub assembly with a certain syringe, an amount of botulin toxin may remain inside the syringe and/or the needle hub assembly after completely inserting the plunger into the barrel of the syringe. Since botulinum toxin is a rather expensive product, it is desirable that only as little as possible botulinum toxin remains inside the needle hub assembly and/or the syringe.

Therefore, it is an object of the present invention to provide for an improved needle hub assembly for use on a syringe that enables improved emptying of the syringe and/or the needle hub during administering of the botulinum toxin to a patient.

To this end, a first aspect of the invention is directed to a needle hub assembly for a syringe, said assembly having a longitudinal axis. The needle hub assembly may comprise a needle hub body having a syringe connector for receiving an attachment member of a syringe at a first end of the body and a needle receiving portion at a second opposing end of the body. The needle hub assembly may also comprise a needle extending from the needle receiving portion. The syringe connector may comprises a substantially conical receiving opening for receiving a syringe attachment member, at least a distal end thereof, wherein the length of said opening, measured along the longitudinal axis is between 3-7 mm, preferably approximately 6.1 +0.05 mm.

The needle hub assembly according to the invention does not strictly comply with the relevant ISO standard ISO594-1. According to said ISO standard, the length of the receiving opening is of sufficient length to ensure proper engagement of the needle hub assembly to the attachment member of the syringe. However, applicant found that the engagement of the needle hub assembly with a syringe, when the length of the receiving opening has the above indicated dimension, is adequate. In order to further enhance the extent of engagement, the needle hub body may be made of a material that has a greater hardness than the material of the syringe to be used. Using harder material provides for a further reduced disengagement risk of the needle hub assembly. However, it is noted that the needle hub body may instead be of a material with a hardness similar to the material of the syringe. The extent of engagement between said parts, when complying with the above indicated length of the receiving opening according to the invention, is sufficient for a proper functioning of the syringe.

With the needle hub assembly according to the invention, when connected to a syringe in order to administer botulinum toxin to a patient, substantially no, or at least as little as possible, toxin is left in the syringe and/or needle hub assembly after completely sliding the plunger into the barrel of the syringe. Since no, or at least as little as possible, toxin is left in the syringe substantial cost savings may be obtained.

According to a further aspect of the invention, a syringe having a longitudinal axis may be provided, wherein the syringe is provided with a needle hub assembly as presently disclosed. The syringe may comprise a barrel extending longitudinally between a proximal end and a distal end of the syringe, said barrel comprising an attachment member for attaching to the needle hub assembly. The syringe may further comprise a plunger that is slidably received in the barrel, wherein the plunger comprises a sealing element that is arranged at a distal end of the plunger and configured to at least cooperate with an inner side of the attachment member. The syringe connector, the attachment member and the sealing element may be configured to cooperate such that, when the plunger is completely inserted in the barrel, a space enclosed by the syringe connector, the attachment member and the sealing element has a volume that is less than 30 μl. Preferably, the space has a volume that is between 4 μl and 30 μl. For instance, the space may have a volume that is less than 14 μl. By optimally gearing the designs and dimensions of the syringe connector, the attachment member and the sealing element to another, an enclosed space is obtained with a volume that approaches zero. With such syringe, the amount of botulinum toxin left in the syringe after administering the injection, is minimized. Applicant has found that with the above described syringe a reduction of approximately 86% of botulinum toxin losses can be obtained in comparison with the use of a standard syringe with a standard needle hub assembly. Optimally, the enclosed space may have such a volume that zero fluid is left in said volume after inserting the plunger completely in the barrel.

Since during treatment with botulinum toxin, a patient is subjected to multiple injections, providing a 20G-35G needle, for example a 33G needle, to the needle hub assembly as presently disclosed, adds to minimizing the trauma for the patient during said injections.

The aforementioned and other features and advantages of the invention will be more fully understood from the following detailed description of certain embodiments of the invention, taken together with the accompanying drawings, which are meant to illustrate and not to limit the invention.

BRIEF DESCRIPTION OF THE DRAWINGS

It is noted that identical or corresponding elements in the different drawings are indicated with identical or corresponding reference numerals.

DETAILED DESCRIPTION

Figure 1:
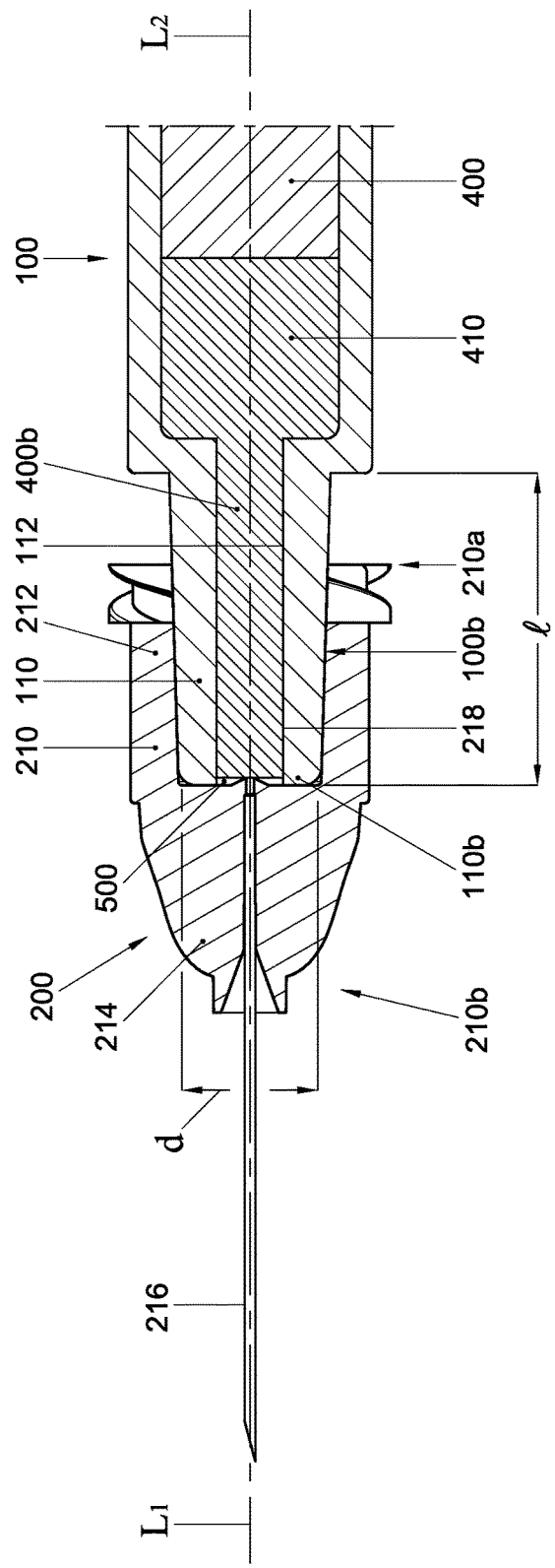
FIG. 1 shows a schematic cross sectional view of an exemplary embodiment of a needle hub assembly according to the present invention.
Figure 2:
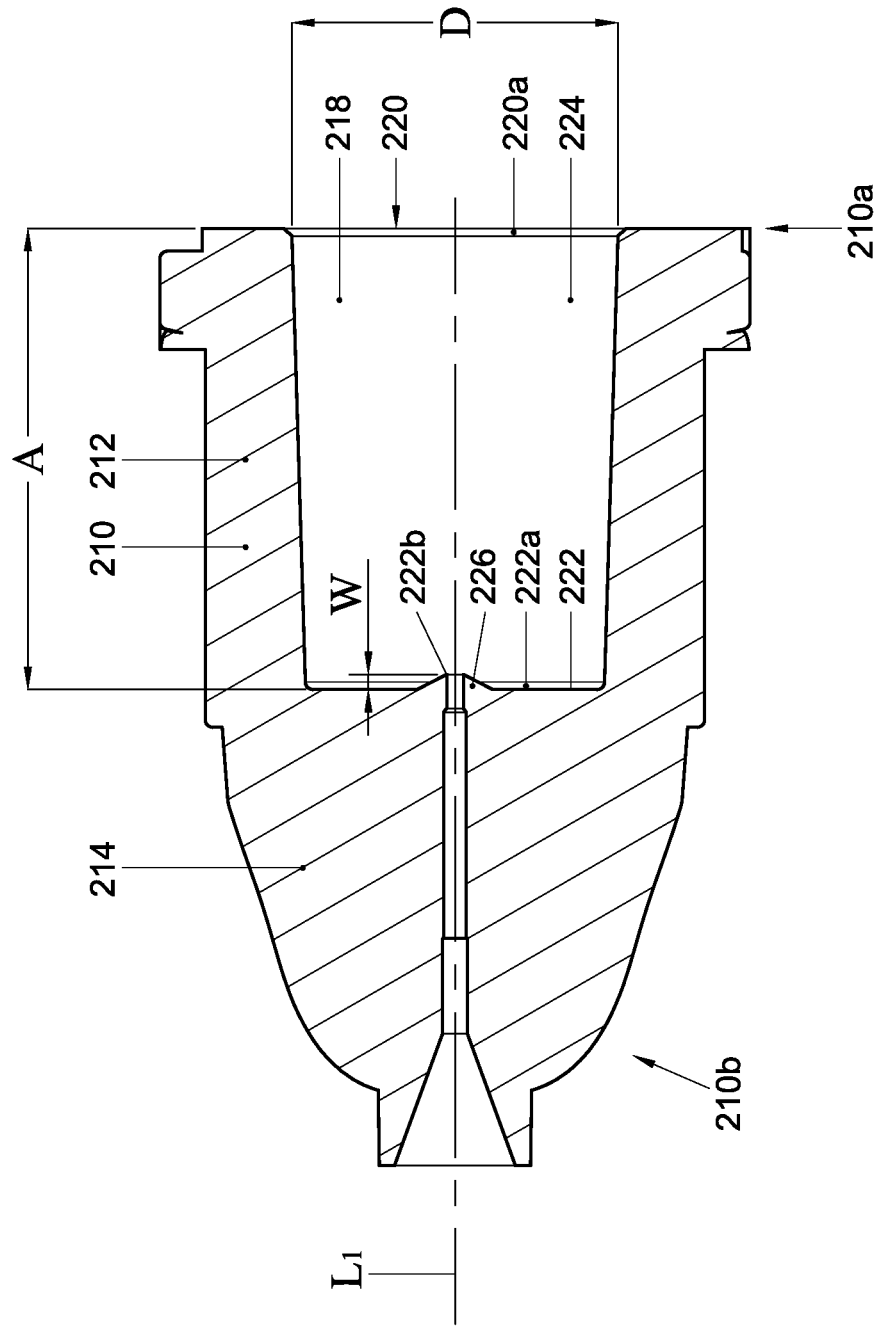
FIG. 2 shows a schematic cross sectional view of a needle hub body of the needle hub assembly shown in FIG. 1.
Figure 3:
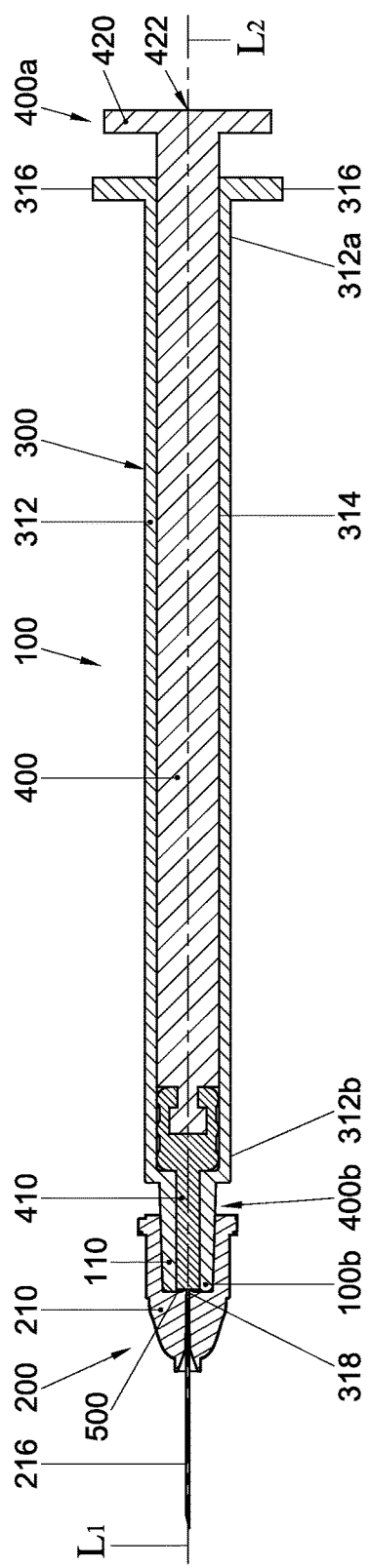
FIG. 3 shows a cross sectional view of a syringe comprising the needle hub assembly shown in FIG. 1

FIGS. 1-3 schematically illustrate an exemplary embodiment of a needle hub assembly 200 and a syringe 100 comprising such assembly 200 according to the present invention. Below, the presently disclosed syringe 100 with the needle hub assembly 200 will be described in general terms, where appropriate with reference to FIGS. 1-3.

The needle hub assembly 200 according to the presently disclosed invention is configured to cooperate with a syringe 100 suitable for injection of fluids in medical applications and the dosing of chemicals in non-medical applications. The needle hub assembly 200 is for instance suitable for injecting botulinum toxin into subcutaneous tissue.

The needle hub assembly 200 has a longitudinal central axis L1. The needle hub assembly may comprise a needle hub body 210 having a syringe connector 212 for receiving an attachment member 110 of the syringe 100. The syringe connector 212 is provided at a first end 210a of the needle hub body 210. At a second, opposing, end 210b of the needle hub body 210 a needle receiving portion 214 may be provided. The needle receiving portion 214 is configured to receive and hold a hypodermic needle 216. The needle 216 extends from the needle hub body 210 in a direction substantially parallel to the longitudinal axis L1 of the hub assembly 200. In the depicted embodiment, the needle 216 may for instance be a 33G×13 needle 216. Preferably, 20G-35G needles may be received in the needle receiving portion 214. A 33G needle 216 is a very thin needle with a cross sectional dimension of approximately 0.2 mm. Therefore, when using such needle 216, the trauma to a patient during injecting the botulinum toxin into the determined tissue is relatively low. Since with a botulinum toxin treatment the patient may be subjected to multiple injections and since the injections may need to be repeated after a while due to the diminishing effect of said botulinum toxin treatment, using such a thin needle 216 decreases the discomfort to a patient.

The needle hub body 210 may be of a material with a greater hardness than the material of the syringe 100. The needle hub body 210 may for instance be of a polycarbonate.

The syringe connector 214 may include a substantially conical receiving opening 218 as is clearly visible in FIG. 2. The receiving opening 218 may be adapted to receive a syringe attachment member 110, at least a distal end 110b thereof. A length A of said receiving opening 218 (see FIG. 2), measured along the longitudinal axis L1, may be between 3-7 mm, in the shown embodiment approximately 6.1 +0.05 mm. The attachment member 110 receiving opening 218 may comprise an entrance area 220, an upper surface 222 and an inner circumferential wall 224 that extends between an entrance area perimeter 220a and an upper surface perimeter 222a. The inner circumferential wall 224 may taper from the entrance area 220 towards the upper surface 222 with approximately 6%. Preferably, the entrance area 220 of the receiving opening 218 has, at the most proximal end 210a of the needle hub body 210, a cross sectional dimension D of 4.315-0.045 mm. In the centre 222b of the upper surface 222, a convex centre part 226 is provided that has a width W that extends from said upper surface 222 approximately 0.2 mm along the longitudinal axis L1 in a direction away from the needle 216.

As is visible in FIG. 3, the syringe 100 may include a barrel 300 and a plunger 400. The barrel 300 may include an elongate tubular, e.g. cylinder jacket-shaped, body 312 that extends along a longitudinal axis L2 of the syringe 100, between a proximal end 312a and a distal end 312b, and that defines a central bore 314 in which the plunger 300 is at least partially slidably and rotatably receivable. At its proximal end 312a, the barrel body 312 may be provided with two finger wings 316 to allow a clinician to press an extended plunger 400 into the bore 314 of the barrel 300 with a thumb, while supporting two fingers distally against the finger wings 316 in a conventional manner of syringe operation. In another, not shown exemplary embodiment, the barrel 300 may include a collar. The barrel 300 and the collar may be manufactured separately and optionally releasably connected first during assembly, or be integrally formed. Both the barrel 300 and the collar may be made from plastic, for instance from a polypropylene by means of injection moulding. The finger wings 316 may also serve to facilitate attachment of the collar to the barrel body 312. At the distal end 312b of the barrel body 312, the central bore 314 may end in a fluid port 318 through which fluid may be drawn into and/or ejected from the bore 314. The distal end 312b of the barrel body 312 itself may taper into a hollow tip, which may provide the attachment member 110 for attaching the needle hub assembly 200 thereto. The attachment member 110 may be a Luer-Slip tip, as shown in the Figures.

The barrel body 312 of the syringe 100 shown in the Figures is opaque. In different embodiments, however, the barrel body 312 may be transparent to enable a clinician to visually assess the contents of the barrel bore 314, for instance to confirm a state/condition or identity of a fluid contained therein. In embodiments featuring a transparent barrel body 312, the barrel body 312 may be provided with a volume graduation, for instance in milliliters.

The plunger 400 may include a sealing element 410 and a handle 420. The sealing element 410, which may be made of a suitably flexible and fluid impermeable material, may be attached to a distal end 400b of the plunger 400, and be dimensioned to enable slidable, sealing contact with an inner wall of the central bore 314 of the barrel 300. The fluid port 318, an inner wall of the central bore 314 and the sealing element 410 may thus delimit a portion of the central bore 314 that serves as a fluid chamber configured to contain a fluid to be delivered by the syringe 100. The size of the fluid chamber may be varied by slidably displacing the plunger 400 relative to the barrel 300. This way, the fluid chamber can be varied in size from nearly the entire volume of the central bore 314 to approximately zero.

The handle 420 of the plunger 400 may be provided at the proximal end 400a of the plunger 400, and, at its proximal end 400a, provide a support surface 422 for a finger or thumb.

A longitudinal sliding motion of the plunger 400 in and relative to the barrel 300 may increase or decrease the volume of the fluid chamber, and thus enable aspiration or ejection of fluid into or from the barrel bore 314.

The syringe connector 218, the attachment member 110 and the sealing element 410 may be configured to cooperate such that, when the plunger 400 is completely slid into the barrel 300, a space 500 enclosed by the syringe connector 218, the attachment member 110 and the sealing element 410 may have a volume that is less than 30 μl. Preferably, the space 500 may have a volume between 4 μl and 30 μl for example approximately less than 14 μl. Furthermore, the distal end 400b of the plunger 400 has a substantially elongate shape that extends through the attachment member 110 such that the distal end 400b of the plunger 400, in an inserted position, substantially completely occupies an inner space 112 of the attachment member 110. Consequently, the syringe 100 including the needle hub assembly 200 provides a substantially zero dead space dosage device that enables minimizing the toxin loss that usually may occur when injecting botulinum toxin. Since the needle hub body 210 material, i.e. polycarbonate, may be harder than the material of the syringe 100, i.e. polypropylene, disconnection of the needle hub body 210 from the attachment member 110 may be prevented. The attachment member 110 may have a length 1 of at least 7.5 mm, preferably of 9±0.3 mm. The diameter d of the distal end 110b of the attachment member 110 is approximately 3.900-4.000 mm.

The syringe 100 may be part of a kit, for instance a sterilized kit, comprising a packaging such as a hard shell blister packaging. Such a packaging may contain a syringe 100 and at least one needle hub assembly 200 according to the described exemplary embodiment.

Although illustrative embodiments of the present invention have been described above, in part with reference to the accompanying drawings, it is to be understood that the invention is not limited to these embodiments. In the present application use of the needle hub assembly for a syringe that is used to inject botulinum toxin has been described. However, the needle hub assembly for a syringe and a syringe comprising such needle hub assembly according to the invention may also be used to advantage to inject other fluids. Variations to the disclosed embodiments can be understood and effected by those skilled in the art in practicing the claimed invention, from a study of the drawings, the disclosure, and the appended claims Reference throughout this specification to "one embodiment" or "an embodiment" means that a particular feature, structure or characteristic described in connection with the embodiment is included in at least one embodiment in the present invention. Thus, the appearances of the phrases "in one embodiment" or "in an embodiment" in various places throughout this specification are not necessarily all referring to the same embodiment. Furthermore, it is noted that particular features, structures or characteristics of one or more embodiments may be combines in any suitable manner to form new, not explicitly described embodiments.

The invention claimed is:

1. A needle hub assembly for a syringe, said assembly having a longitudinal axis comprising:
   a needle hub body having a syringe connector for receiving an attachment member of a syringe at a first end of the body and a needle receiving portion at a second opposing end of the body,
   a needle extending from the needle receiving portion,
   wherein the syringe connector comprises a substantially conical receiving opening for receiving a syringe attachment member, at least a distal end thereof, wherein a length of said opening, measured along the longitudinal axis, is between 3-7 mm.

2. The needle hub assembly according to claim 1, wherein an upper surface of the receiving opening of the syringe connector comprises a convex center part extending from the upper surface approximately 0.2 mm along the longitudinal axis in a direction away from the needle.

3. The needle hub assembly according to claim 1, wherein an entrance area of the receiving opening has a cross sectional dimension of approximately 4.315-0.045 mm.

4. The needle hub assembly according to claim 1, wherein an inner circumferential wall of the receiving opening that extends between an entrance area perimeter and an upper surface perimeter tapers from the entrance area towards the upper surface with 6%.

5. The needle hub assembly according to claim 1, wherein the syringe connector comprises a 6% Luer taper.

6. The needle hub assembly according to claim 1, wherein the needle is one of a 20G-35G needle.

7. A syringe comprising a needle hub assembly according to claim 1, wherein the syringe, having a longitudinal axis, comprises:
   a barrel extending longitudinally between a proximal end and a distal end of the syringe, said barrel comprising an attachment member for attaching to the needle hub assembly and
   a plunger that is slidably received in the barrel, the plunger comprising a sealing element that is arranged at a distal end of the plunger and configured to at least cooperate with an inner side of the attachment member,
   wherein the syringe connector, the attachment member and the sealing element are configured to cooperate such that, when the plunger is completely inserted in the barrel, a space enclosed by the syringe connector, the attachment member and the sealing element has a volume that is less than 30 μl.

8. The syringe according to claim 7, wherein the space has a volume that is between 4 μl and 30 μl.

9. The syringe according to claim 7, wherein the material of the needle hub body has a greater hardness than the material of the syringe, at least than the material of the attachment member of the syringe.

10. The syringe according to claim 7, wherein the syringe, or at least the attachment member of the syringe, is of polypropylene and the needle hub body is of polycarbonate.

11. The syringe according to claim 7, wherein a length of the attachment member is at least 7.5 mm.

12. The syringe according to claim 7, wherein a diameter of the distal end of the attachment member is 3.900-4.000 mm.

13. The syringe according to claim 7, wherein the distal end of the plunger has a substantially elongate shape to extend through the attachment member such that the distal end of the plunger, in an inserted state, substantially completely occupies an inner space of the attachment member.

14. A syringe and a needle hub assembly kit comprising a packaging that houses a syringe and at least one needle hub assembly according to claim 1.

15. The syringe and needle hub assembly kit according to claim 14, wherein the packaging is a hard shell blister packaging.

16. The syringe according to claim 11, wherein the length of the attachment member is 9±0.3 mm.

17. The needle hub assembly of claim 1, wherein the longitudinal axis is approximately 6.1±0.05 mm.

18. The needle hub assembly of clam 6, wherein the needle is a 33G×13 mm needle.

\* \* \* \* \*

UNITED STATES PATENT AND TRADEMARK OFFICE
CERTIFICATE OF CORRECTION

PATENT NO. : 9,913,949 B2
APPLICATION NO. : 15/028559
DATED : March 13, 2018
INVENTOR(S) : Isodoris Angelinus Quirinus Maria de Beer It is certified that error appears in the above-identified patent and that said Letters Patent is hereby corrected as shown below:

In Column 7, Line 12, in Claim 17, delete "6.1±0.05 mm." and insert --6.1+0.05 mm.-- therefor Signed and Sealed this
Eleventh Day of December, 2018

Andrei Iancu
*Director of the United States Patent and Trademark Office*